United States Patent [19]
Knapp, Jr. et al.

[11] Patent Number: 5,762,966
[45] Date of Patent: Jun. 9, 1998

[54] TISSUE GRAFT AND METHOD FOR URINARY TRACT UROTHELIUM RECONSTRUCTION AND REPLACEMENT

[75] Inventors: Peter M. Knapp, Jr.; James E. Lingeman, both of Indianapolis; Robert J. Demeter, Morrisville; Stephen F. Badylak, W. Lafayette, all of Ind.

[73] Assignees: Purdue Research Foundation, West Lafayette, Ind.; Methodist Hospital of Indiana, Indianapolis, Ind.

[21] Appl. No.: 784,117

[22] Filed: Jan. 15, 1997

Related U.S. Application Data

[62] Division of Ser. No. 632,756, Apr. 16, 1996, Pat. No. 5,645,860, which is a continuation of Ser. No. 418,516, Apr. 7, 1995, abandoned.

[51] Int. Cl.$^6$ .................................................. A61K 35/38
[52] U.S. Cl. ............................. 424/551; 623/11; 623/12
[58] Field of Search ............................. 424/551; 623/12, 623/11

[56] References Cited

U.S. PATENT DOCUMENTS

| | | | |
|---|---|---|---|
| 2,127,903 | 8/1938 | Bowen | 606/154 |
| 3,562,820 | 2/1971 | Braun | 3/1 |
| 4,902,508 | 2/1990 | Badylak et al. | 424/551 |
| 4,956,178 | 9/1990 | Badylak et al. | 424/551 |
| 5,275,826 | 1/1994 | Badylak et al. | 424/551 |
| 5,281,422 | 1/1994 | Badylak et al. | 424/551 |
| 5,352,463 | 10/1994 | Badylak et al. | 424/551 |
| 5,372,821 | 12/1994 | Badylak et al. | 424/551 |

FOREIGN PATENT DOCUMENTS

WO 95/06439  3/1995  WIPO.

OTHER PUBLICATIONS

"Comparison of Bovine Collagen Xenografts to Autografts in the Rabbit", J.C. Tauro, et al., *Clinical Orthopaedics and Related Research*, No. 266, May, 1991. pp. 271–284.

"Development of a Reconstituted Collagen Tendon Prosthesis", Jack D. Goldstein, et al., *The Journal of Bone and Joint Surgery, Incorporated*, vol. 71–A, No. 8, Sep. 1989, pp. 1183–1191.

"Replacement of Dog's Aorta by Autologous Intestinal Muscle in the Infected Retroperitoneum", R. Broll, et al., Eurp. Surg. Res., 18:390–396 (1986).

"Aortic Replacement with Multi-Layer Submucosa Prostheses Made From Heterologous Small Intestine", G. Rotthoff, et al., presented at 8th Congress of the International Society of Cardiovascular Surgery, Vienna, Sep. 7–9, 1967.

"Replacement of the Abdominal Aorta by an Ieum Muscle Tube in an Animal Experiment", J. Huth, et al., (translation), *Thoraxchir. Vask, Chir.*, 15(4):401–407, Aug. 1967.

"Long Term Observations and Histological Studies on Vessel and Heart Wall Grafts From Small Intestine", R. Haring, et al., (translation),*Langenbecks Arch. Klin. Chir.*, 1965, 313:664–8.

"Replacement of the Abdominal Aorta With A Small–Intestine Muscle Tube In An Animal Experiment", J. Huth, (translation), *Zentralbl Chir.*, 92(26/2): 1817–19 (1967).

"Reconstruction of the Arterial Flow Path by Autologous Intestinal Muscle Grafts in The Dog", H.P.Bruch, et al., (translation), *Folia Angiologica*, vol. 29 (3–5/81) pp. 65–68.

"Replacement of the Aorta by Multilayered Submucosa Protheses of Heterologous Ileum", G. Rotthoff, et al., (translation), *Bulletin de la Societe International de Chirurgie*, No. 2, 1969, 256–259.

"Biocompatibility of Small–Intestinal Submucosa in Urinary Tract as Augmentation Cystoplaty Graft and Injectable Suspension", Journal of Endourology, vol. 8, No. 2, pp. 125–130, Apr. 12, 1994.

*Primary Examiner*—Jean C. Witz
*Attorney, Agent, or Firm*—Barnes & Thornburg

[57] ABSTRACT

A method for surgical repair of a diseased or damaged bladder is described. Diseased or damaged bladder tissue is surgically replaced with submucosal tissue of a warm blooded vertebrate to promote regrowth of endogenous urinary bladder tissue.

8 Claims, No Drawings ered submucosal matrices as a urinary bladder graft.
TISSUE GRAFT AND METHOD FOR URINARY TRACT UROTHELIUM RECONSTRUCTION AND REPLACEMENT This is a division of U.S. application Ser. No. 08/632, 757, filed Apr. 16, 1996 now U.S. Pat. No. 5,645,060 which is a continuation of U.S. application Ser. No. 08/418,516, filed Apr. 7, 1995, now abandoned.

FIELD OF THE INVENTION

The present invention relates to a tissue graft and method for repairing damaged or diseased urinary bladder. More particularly, this invention is directed to a method for promoting growth of endogenous bladder tissues to replace surgically removed bladder defects.

BACKGROUND AND SUMMARY OF THE INVENTION

Urologists have long been searching for an alloplastic or biodegradable material suitable for use as a urinary bladder replacement graft. Many experiments have been conducted utilizing synthetic biomaterials such as silicone rubber, polytetrafluoroethylene and polypropylene for bladder reconstruction. Such materials have been found generally to induce foreign body-type reactions resulting in the rejection or mineralization of the graft.

The reported failures of experiments with synthetic biomaterials, have led researchers to investigate the use of natural or synthetic biodegradable materials, such as gastrointestinal, placental, amniotic and pericardial tissues and synthetic resorbable polymers, for bladder regeneration. These materials serve as a scaffold for endogenous cell growth, but dissolve prior to the onset of any foreign body-type reactions. In particular gastrointestinal tissue has been a preferred source of material for bladder reconstruction. However, the use of gastrointestinal tissue in bladder reconstruction has been associated with deleterious side effects such as infection, intestinal obstruction, mucus production, electrolyte abnormalities and carcinogenicity.

Placental, amniotic and pericardial tissue grafts are useful as graft materials for replacing urinary bladder tissue however, such graft materials suffer the disadvantage of graft shrinkage, and they fail to promote complete bladder wall regeneration (tissue having a urine impermeable layer and a functional muscle cell layer).

Clearly a tissue graft material is desired which is non-immunogenic, which is not subject to gross shrinkage after implantation, and which promotes the growth of endogenous urinary bladder tissues having a urine impermeable cell layer and a functional muscle cell layer.

The present invention is directed to the use of vertebrate submucosa matrices for promoting the replacement of damaged or diseased portions of a urinary bladder with endogenous urinary bladder tissue. The collagenous submucosa tissue used in accordance with the present invention comprise highly conserved collagens, glycoproteins, proteoglycans, and glycosaminoglycans in their natural configuration and natural concentration. Submucosal tissue can be obtained from various sources, including particularly intestinal tissue harvested from animals raised for meat production, including, for example, pigs, cattle and sheep or other warm-blooded vertebrates. This tissue can be used in either its natural configuration or in a comminuted or partially digested fluidized form. Vertebrate submucosal tissue is a plentiful by-product of commercial meat production operations and is thus a low cost tissue graft material, especially when the submucosal tissue is used in its native sheet configuration.

It is known that compositions comprising the tunica submucosa and the basilar portions of the tunica mucosa of the intestine of warm-blooded vertebrates can be used as tissue graft materials in sheet form. See U.S. Pat. No. 4,902,508. The compositions described and claimed in that patent are characterized by excellent mechanical properties, including high compliance, a high burst pressure point, and an effective porosity index which allowed such compositions to be used beneficially for vascular graft constructs. The graft materials disclosed in that patent are also useful in tendon, ligament and other connective tissue replacement applications. When used in such applications the preferred graft constructs appear to serve as a matrix for the regrowth of the tissues replaced by the graft constructs. Intestinal submucosal tissue has undergone extensive immunologic testing in over 600 cross-species implants and has never been shown to elucidate a rejection reaction.

Furthermore, it is known that intestinal submucosa can be fluidized by comminuting and/or protease digestion, without loss of its apparent biotropic properties, for use in less invasive methods of administration (e.g., injection or topical) to host tissues in need of repair. See U.S. Pat. No. 5,275,826. Fluidized comminuted intestinal tissue comprising tunica submucosa has previously been successfully used to repair and functionally augment damaged tissues including, for example, urinary bladder sphincter. Common events to tissue remodeling include widespread and rapid neovascularization, proliferation of granulation mesenchymal cells, biodegradation of implanted submucosal tissue, and lack of immune rejection.

The present invention is directed to the use of vertebrate-derived submucosal matrices as a urinary bladder graft. Submucosal tissue is an inexpensive, nonimmunogenic material that induces host tissue proliferation, remodeling and regeneration of urinary bladder tissues upon implantation. In accordance with this invention tissue graft constructs comprising submucosal tissue of a warm-blooded vertebrate have been found to promote the growth of endogenous urinary bladder tissues having both a urine impermeable cell layer and a function muscle cell layer.

Thus in accordance with the present invention, there is provided a method for reconstructing a diseased or damaged urinary bladder. The method comprises the steps of surgically removing the damaged or diseased portion and replacing the removed portion with a tissue graft construct comprising submucosal tissue of a warm-blooded vertebrate.

DETAILED DESCRIPTION OF THE INVENTION

There is provided in accordance with the present invention a method and composition for replacing damaged or diseased urinary bladder tissues. The submucosal graft compositions of the present invention function as a biotropic/biodegradable scaffold that induces endogenous tissues to invade and replace the graft material with endogenous urinary bladder tissue.

The submucosal tissue of the present tissue graft constructs is derived from vertebrate submucosa and comprises naturally associated extracellular matrix proteins, glycoproteins and other factors. In one embodiment the submucosal tissue comprises intestinal submucosal tissue of a warm-blooded vertebrate. The small intestine of warm-blooded vertebrates is a preferred source of submucosal tissue for use in this invention.

Intestinal-derived submucosal tissue for use in this invention comprises the tunica submucosa delaminated from both the tunica muscularis and at least the luminal portion of the tunica mucosa. In one embodiment of the present invention the intestinal submucosal tissue comprises the tunica submucosa and a basilar portion of the tunica mucosa, which can include the lamina muscularis mucosa and the stratum compactum which layers are known to vary in thickness and in definition dependent on the source vertebrate species.

The preparation of submucosal tissue for use in accordance with this invention is described in U.S. Pat. No. 4,902,508, the disclosure of which is expressly incorporated herein by reference. A segment of vertebrate intestine, preferably harvested from porcine, ovine or bovine species, but not excluding other species, is subjected to abrasion using a longitudinal wiping motion to remove the outer layers, comprising smooth muscle tissues, and the innermost layer, i.e., the luminal portion of the tunica mucosa. The submucosal tissue is rinsed with saline and optionally sterilized; it can be stored in a hydrated or dehydrated state. Lyophilized or air dried submucosa tissue can be rehydrated, optionally stretched, and used in accordance with this invention without significant loss of its cell proliferative activity.

In one embodiment in accordance with the present invention, several strips of submucosal tissue can be adhered to one another to form a large area, submucosal sheet. The process of forming large area submucosal sheets involves cutting strips of submucosal tissue and overlapping at least a portion of each strip with a portion of an adjacent strip. The overlapped portions are then compressed under dehydrating conditions to form a large sheet of submucosal tissue. In one embodiment the strips of submucosal tissue are layered onto a permeable surface and a second optionally permeable surface is used to compress the overlapped portions between the two surfaces.

Optionally the large area sheet of submucosal tissue can be formed from multiple layers of submucosal tissue strips. In one embodiment submucosal tissue strips are organized on a mesh in one direction with at least a portion of one strip of submucosal tissue overlapping with at least a portion of another strip of submucosal tissue. Once the mesh is covered with one layer of submucosal tissue a second layer of submucosal tissue is applied on top of the first layer but at a different angel relative to the first layer. Additional layers of submucosal tissue can be added to obtain a graft construct having a desired strength or thickness. After all the strips of submucosal tissue are placed on the mesh, another mesh is placed on top of the submucosal tissues and the "mesh-submucosal tissue-mesh" sandwich is compressed with a load and dried. This process produces a dried large area submucosal sheet that can be pealed off the mesh.

In one embodiment the submucosal tissue construct is formed from two or more strips of submucosal tissue pressed together and dried through the use of vacuum bagging. In that method submucosal tissue is laid out between two perforated, preferably stainless steel, plates. The plates are shaped to define the desired shape, e.g. a pouch construct, for the bladder replacement graft. The material is optionally placed on a surface and covered with blotting material to soak up water, and a breather blanket to allow air flow. The resulting "sandwich" of pressure plates and submucosal tissue is then sealed into a nylon bag that has a vacuum port. A vacuum is applied to pull air out of the vacuum bag and the resulting drop in atmospheric pressure compresses the plates against the submucosal tissue and simultaneously, at least partially, dehydrates the submucosal tissue. After 4 to 24 hours of applying a vacuum, the produced sheet is still moist and very flexible. No seams from the layering of the submucosal tissue are visible and the strength of a prototype 8-thickness sheet as determined by ball burst test is approximately 80 pounds. This general procedure can also be used to shape single submucosa tissue strips for use in this invention, if "shaping" of such single layer submucosa constructs is determined to be necessary or appropriate for particular surgical application.

Alternatively, large area sheets of submucosal tissue can be formed from smaller segments of submucosal tissue through the use of sutures and/or the use of binder pastes as described in U.S. Pat. No. 3,562,820, the disclosure of which is expressly incorporated herein by reference.

The mechanical properties of the large area submucosal sheet can be altered by adjusting the number of layers in the sheet, varying the angle of adjacent layers to each other, and varying the load applied to press the submucosal strips into a large area submucosal sheet.

The submucosal tissue grafts of the present invention can be preconditioned by stretching the material in a longitudinal or lateral direction as described in U.S. Pat. No. 5,275,826, the disclosure of which is expressly incorporated herein by reference. The submucosal material can be stretched prior to the formation of the graft constructs or during the formation of the constructs, or the submucosal tissue can be stretched after formation of the sheets.

The graft compositions of the present invention can be sterilized using conventional sterilization techniques including glutaraldehyde tanning, formaldehyde tanning at acidic pH, ethylene oxide treatment, propylene oxide treatment, gas plasma sterilization, gamma radiation, electron beam and peracetic acid sterilization. Sterilization techniques which do not adversely affect the mechanical strength, structure, and biotropic properties of the submucosal tissue is preferred. For instance, strong gamma radiation may cause loss of strength of the sheets of submucosal tissue. Preferred sterilization techniques include exposing the graft to peracetic acid, 1-4 Mrads gamma irradiation (more preferably 1-2.5 Mrads of gamma irradiation) or gas plasma sterilization; peracetic acid sterilization is the most preferred sterilization method. Typically, the submucosal tissue is subjected to two or more sterilization processes. After the submucosal tissue is sterilized, for example by chemical treatment, the tissue may be wrapped in a plastic or foil wrap and sterilized again using electron beam or gamma irradiation sterilization techniques.

In accordance with the present invention, submucosal tissue is used as a tissue graft for replacing/reconstructing damaged or diseased urothelial tissue of the urinary tract. Urothelial tissue is defined herein as including the cells and tissues of the ureter, urethra and renal collection system. The submucosal graft constructs promote the growth of endogenous urothelial tissues upon implantation into a host organism. These graft constructs can be used to replace large sections of the ureter, uretha and urinary bladder.

In one embodiment, the submucosal tissue graft constructs are surgically implanted to promote the growth of endogenous urinary bladder tissues having a urine impermeable cell layer and a functional muscle cell layer. The tissue graft material serves as a scaffold and induces the proliferation of functional urinary bladder tissue formation which replaces the tissue graft without shrinkage of the graft area or formation of "scar" tissue.

As mentioned above, the tissue graft construct can be formed in the shape of a pouch to assist in the replacement of large portions (i.e. greater than 20%) of the urinary bladder. The construct can be formed by surgical construction from one or more submucosal strips or by a compression-forming procedure such as that described above. Furthermore the tissue graft construct can be manipulated to form ports in the tissue graft for surgical attachment and fluid communication with the ureters and the urethra.

The tissue graft constructs of the present invention can be implanted into a vertebrate host species to repair a damaged, diseased or otherwise functionally compromised urinary bladder. In one embodiment the defective portion of the bladder is surgically removed and replaced with a tissue graft construct comprising submucosal tissue of a warm-blooded vertebrate. Where the submucosal tissue is of intestinal origin it is preferred that the luminal side of the intestinal submucosal tissue is directed toward the bladder lumen. Large portions of the bladder can be removed and replaced with the tissue grafts of the present invention. After implantation, the constructs are eventually remodelled by the host with functional urinary bladder tissues having a stratification of cell layers similar to that found in the normal urinary bladder wall. It is anticipated that the entire urinary bladder can be replaced with the present graft construct to regenerate a functional urinary bladder.

In vivo experiments have been conducted in pigs, dogs and rats to investigate the efficacy of submucosal tissue as an augmentation cystoplasty graft (see examples 2, 3 and 4). These experiments confirm the efficacy of the present graft constructs for urinary bladder reconstruction. Morphologic examination of the urinary bladders from those experiments show that there was a clear remodeling of the tissue with minimal or no adhesions to the surrounding abdominal structures. Additionally, a smooth transitional epithelial cell layer was formed on the luminal surface creating a urine impermeable layer that retains urine.

The present experiments demonstrate that at least 70% of the original urinary bladder tissue can be removed and remodeled using the submucosal tissue grafts of the present invention. Thus only a small portion of the original urinary bladder tissue is required to be left while remodelling occurs. The source of the cells forming the smooth muscle cells of the urinary bladder has not been determined but likely represents mobilization of cells from the surrounding smooth muscle of the remaining urinary bladder, as well as circulating mononuclear cells that arrive at the site via the blood stream and differentiate into smooth muscle cells.

Histological data obtained from the rat bladder replacement studies revealed that transitional epithelium completely covered the submucosal tissue patch graft by two weeks post operative. Significant acute inflammatory response did not occur at any time during host remodeling. Host remodeling occurred primarily from mononuclear and fibroblastic cellular invasion from the periphery (2 weeks) which migrated toward the center (4 weeks) of the graft and was eventually replaced completely by native host tissue 3 months after implantation. Smooth muscle fibers, although sparse, were present at 4 weeks, and became fully organized and indistinguishable from normal bladder smooth muscle fibers at 11 months. Histologically, these findings imply that the cellular reaction represents a fibrovascular healing type reaction, and the mononuclear cellular infiltrate represented digestion of the submucosal collagen and its replacement by native collagen.

One complication associated with the use of foreign material in the urinary tract is the formation of calculi (the formation of inorganic masses, i.e. mineral salts or "kidney stones"). Although calculi were present in a majority of the animals harvested after 3 months, they were free floating and not adherent to graft. Because stone analysis revealed hydroxyapatite and not struvite, an infectious cause for the calculi is reduced. A review of the previously published long term augmentation studies in rats also revealed bladder calculi present in their control group, gastrocystoplasty group, ileocystoplasty group, and colocystoplasty group. Bladder stone formation also been reported in a group of rats that received autoaugmentation. Therefore, it appears that any sort of bladder surgery in the rat predisposes it to stone formation. Given these findings, it appears that the calculi formation was due to the bladder surgery and not directly related to the submucosal graft material itself.

EXAMPLE 1

Preparation of Submucosal Tissue

Small intestine submucosa was prepared in accordance with the procedures described in U.S. Pat. No. 4,902,508. Briefly, sections of porcine jejunum were harvested within ten minutes of euthanasia and immediately placed in 0.9% saline solution. These sections were cut into 10 to 20 cm lengths and the mesenteric tissues were removed from the segment of the small intestine. The small intestine was exerted (inside out) and the tunica mucosa mechanically removed. The small intestinal segment was exerted again (i.e. the stratum compactum on the luminal side, as in the original orientation) and the serosa and tunica muscularis were removed from the outer surface. The tissue was rinsed in saline and placed in a 10% neomycin sulfate solution until used as a graft material. Storage time for the graft material ranged from 2 weeks to 3 months. It should be noted that preparation of submucosal tissue is a mechanical process similar to that of sausage casing and involves no enzymatic reaction steps.

EXAMPLE 2

Surgical Repair of Pig Urinary Bladder

Canine intestinal submucosal tissue was used in the pig as a xenogeneic material. The intestinal submucosal tissue for the graft was used within 1 to 5 days of collection. The intestinal submucosal tissue for injection was prepared by mechanical emulsification of the tissue to enable injection of the suspension through an 18-gauge needle.

Four female pigs were randomly selected for either bladder wall, bladder neck, or periureteral intestinal submucosal tissue injection. Fluidized intestinal submucosal tissue (10–20 mL) was injection through an 18-gauge needle into submucosal or subserosal sites to create a discrete nodule. The injection sites were observed simultaneously through a cystoscope and a laparoscope to ensure that the intestinal submucosal tissue was injection into the bladder wall or submucosa without spillage. Each of the nodules created was documented on videotape. Cystoscopy was performed in the first animal at 2 weeks to confirm persistence of the wheal at the injection site. Bladder specimens were harvested for pathologic examination at 8, 10, 18, 25, and 34 weeks.

Animal No. 2 underwent harvest of a bladder dome injection site at 10 weeks. Following the partial cystectomy, a bladder augmentation was performed using an intestinal submucosal tissue patch graft. The detubularized patch was orientated with the luminal surface of the graft towards the bladder lumen and sutured to the bladder with a watertight closure. The bladder was drained for 3 weeks with a Foley catheter, at which time, the augmentation was examined with cystoscopy, laparoscopy, and cystography. The patch graft appeared to be epithelialized, and bladder capacity was preserved. The Foley catheter was removed. The bladder was harvested 8 weeks after augmentation for histologic examination.

Histological examination of the fluidized intestinal submucosal tissue injection sites did not detect any inflammatory reaction or granuloma formation. Gradual ingrowth of host epithelium, connective tissue, and smooth muscle tissue into the graft material was demonstrated. Connective tissue, smooth muscle and capillary ingrowth were demonstarted as early as 8 weeks after injection.

Cystography of the submucosal patch graft at 3 weeks followed by laparoscopy and cystoscopy demonstrated full capacity of the bladder with no evidence of scar tissue or contracture. The luminal surface was completely epithelialized. Gross examination 8 weeks after augmentation cystoplasty demonstrated maintenance of the original bladder capacity with thickening of the graft site. Complete epithelialization of the luminal surface of the patch graft was confirmed histologically. Dense ingrowth of spindle cells, fibroblasts, and smooth muscle cells could be seen under the epithelium. Alpha smooth-muscle actin-specific staining confirmed the smooth muscle ingrowth into the graft material. Ingrowth of capillaries could also be identified in the patch graft.

EXAMPLE 3
Surgical Repair of Rat Urinary Bladder

Twenty-two male Sprague Dawley rats, weighing between 250 and 300 mg., were anesthetized with nembutal (15 mg/kg) and a midline abdominal incision was made exposing the bladder. The thin attachments of the perivesical fat were sharply freed from the bladder exposing the bladder neck. Four suspensory sutures of 5-0 silk were then placed at the four corners of the bladder for ease of bladder manipulation. Utilizing microscissors, the entire dorsal surface of the bladder (10×10 mm) was excised (approximately one-third of the bladder surface area) and hemostasis obtained with microcautery. A piece of submucosal tissue graft was then fashioned slightly larger than the defect (stratum compactum surface facing the bladder lumen) and sewn into place with 7-0 mild chromic using a continuous, non-interlocking suture. To ensure a competent closure, a dilute methylene blue solution was injected through a 30 gauge needle on the ventral surface of the bladder. Sutured margins from which dye extravasated were oversewn with interrupted 7-0 mild chromic sutures. The submucosal tissue graft borders were then marked with four permanent marking sutures (proline) for future reference as to the exact position of the graft. The abdominal wounds were then closed in two layers with running 5-0 Dexon for both the muscle and skin. Urinary diversion or drains were not used in the immediate postoperative period nor did any of the animals receive antibiotics during the study period.

For histologic evaluation, animals were sacrificed at 2, 4, 8, 12, 24, and 48 weeks post-augmentation and the resected bladders were fixed in buffered 10% formalin solution for at least 24 hours. After fixation, each specimen was bisected in a sagittal plane through the trigone and the grafted region at the dome of the bladder. Both halves were embedded in paraffin. Sections were cut at 5 microns and stained with Massons hematoxylin and eosin, Periodic acid-Schiff, and Massons trichrome stains.

Results

Macroscopically, the inflated bladder specimens were uniformly dilated without evidence of diverticular formation in the region of the graft. The grafts were barely discernible as a slightly whitened area compared to the surrounding native bladder. There were minimal adhesions to the surrounding perivesical fat or other intraabdominal structures. Free floating, tan-brown calculi non-adherent to the graft were noted in the bladders of three of the four animals harvested at twelve weeks, one of two animals harvested at twenty-four weeks, and three of four of the animals harvested at forty-eight weeks. None of the other animals had any evidence of bladder calculi. Routine stone analysis revealed 100% hydroxyapatite. No gross evidence of hydroureteronephrosis was apparent in any of the animals. Two animals died in the early postoperative period secondary to suture line leakage and these animals were replaced to maintain the total number of animals at 22. No other animals were lost throughout the study period.

Histologically, at two weeks, the submucosal tissue grafts were completely covered by transitional epithelium. Grafts showed a prominent vascular proliferation (neovascularization) at their edges and infiltration of their entire surface by fibroblasts and new capillaries. There was a moderately intense mononuclear inflammatory cell response in the periphery. Centrally, the inflammation was less intense, and fibroblasts and small capillaries infiltrated the collagen fibers of the submucosal tissue.

By 4 weeks, the grafts were infiltrated completely by well-formed small blood vessels and fibroblasts. Mononuclear inflammatory cell infiltrates were minimal at the edges but moderately intense in the central region. Myofibers with morphologic and staining characteristics consistent with smooth muscle were scattered throughout the periphery.

At three months, inflammatory activity throughout the graft had subsided, and small but well-formed blood vessels persisted. Collagen was well organized, and scattered fibroblasts were interspersed among the individual collagen fibers. Small myofibers with morphologic and staining properties of smooth muscle were present scattered throughout. In addition, distinct bundles of well-formed smooth muscle now were evident in a small portions of the grafts.

Finally, at 24 and 48 weks post-augmentation all three layers of the normal rat bladder (urothelium, smooth muscle and serosa) were present and grossly and microscopically indistinguishable from the normal rat bladder. The permanent marking sutures delineating the margins of the submucosal tissue graft were the only guide to where the submucosal tissue graft had been surgically implanted and there was no evidence of graft shrinkage. Animals with bladder calculi present had a global urothelial inflammation in both the submucosal tissue regenerated and remaining normal bladder. Animals without calculi had no signs of inflammation.

EXAMPLE 4
Surgical Repair of Dog Urinary Bladder

A dog study comprising fourteen animals was also conducted in which 30–70% of the urinary bladder was replaced by peracetic acid sterilized submucosal tissue material. The animals were sacrificed at 1 week, 2 weeks, 4 weeks, 8 weeks, 12 weeks, 6 months, and 14 months after surgery. In summary, the animals all showed the ability to retain urine, and to urinate normally, within two days of the surgery. The urinary bladders remodeled (the graft tissue was replaced with endogenous urinary bladder tissue) within a very short period of time (1–2 weeks) to contain a normal transitional epithelium, basement membrane, submucosa, and a thinner and normal but definitely organized smooth muscle cell layer. None of the dogs became infected, showed fever, or showed any evidence of rejection of the xenogeneic material.

In vitro studies of the excised tissue at the time of sacrifice shows that the newly remodeled urinary bladder contained contractile and functioning spindle cells (smooth muscle cells) and had neural receptors. These cells reacted in response to carbachol and to nicotine. The carbachol responses were blocked by atropine. Additionally, the smooth muscle cells responded to electrical stimulus at approximately 75% of the normal urinary bladder smooth muscle contractile force.

The volume of the urinary bladder prior to surgery was approximately 51 mls and at the time of sacrifice the urinary bladder volume was approximately 55 mls. Thus the size of the urinary bladder was retained with the use of the submucosal tissue graft material and there was no evidence of shrinkage as would be expected in "scarring".

The ability of the reconstructed urinary bladder to exert pressure was maintained. The pressure producing capabilities of the urine were 52 cm of water prior to surgery and 45 cm of water at the time of sacrifice.

We claim:

1. A tissue graft construct for replacement of damaged or diseased portions of a urinary bladder, said construct comprising a sheet of submucosal tissue of a warm-blooded vertebrate formed as a pouch having ports for surgical attachment and fluid communication with the ureters and the urethra for replacement of 20% or more of the urinary bladder.

2. The tissue graft construct of claim 1 wherein said tissue graft construct is formed from two or more strips of submucosal tissue of a warm-blooded vertebrate, said graft construct having a surface area greater than any one of the individual strips used to form said graft construct.

3. The tissue graft construct of claim 1, wherein the submucosal tissue is intestinal submucosa comprising the tunica submucosa delaminated from both the tunica muscularis and at least the luminal portion of the tunica mucosa.

4. A tissue graft construct for replacement of damaged or diseased portions of a urinary bladder, said construct comprising submucosal tissue of a warm-blooded vertebrate formed as a pouch for replacement of 70% or more of the urinary bladder.

5. The tissue graft construct of claim 4 wherein said pouch has ports for surgical attachment and fluid communication with the ureters and the urethra.

6. The tissue graft construct of claim 4 wherein said tissue graft construct is formed from two or more strips of submucosal tissue of a warm-blooded vertebrate, said graft construct having a surface area greater than any one of the individual strips used to form said graft construct.

7. The tissue graft construct of claim 4, wherein the submucosal tissue is intestinal submucosa comprising the tunica submucosa delaminated from both the tunica muscularis and at least the luminal portion of the tunica mucosa.

8. A tissue graft construct for the replacement of a urinary bladder, said construct comprising submucosal tissue of a warm-blooded vertebrate in the shape of a pouch for replacement of the entire urinary bladder, said pouch having ports for surgical attachment and fluid communication with the ureters and the urethra.

* * * * *